United States Patent
Ray, II

(10) Patent No.: US 10,898,455 B2
(45) Date of Patent: Jan. 26, 2021

(54) UREA CREAM FORMULATIONS

(71) Applicant: CMPD LICENSING, LLC, Conroe, TX (US)

(72) Inventor: Jay Richard Ray, II, Conroe, TX (US)

(73) Assignee: CMPD Licensing, LLC, Conroe, TX (US)

( * ) Notice: Subject to any disclaimer, the term of this patent is extended or adjusted under 35 U.S.C. 154(b) by 0 days.

(21) Appl. No.: 14/990,168

(22) Filed: Jan. 7, 2016

(65) Prior Publication Data

US 2017/0196823 A1 Jul. 13, 2017

(51) Int. Cl.
| | |
|---|---|
| A61K 31/17 | (2006.01) |
| A61K 9/00 | (2006.01) |
| A61K 9/06 | (2006.01) |
| A61K 31/351 | (2006.01) |
| A61K 31/496 | (2006.01) |
| A61K 31/56 | (2006.01) |
| A61K 47/10 | (2017.01) |

(52) U.S. Cl.
CPC ............ *A61K 31/17* (2013.01); *A61K 9/0014* (2013.01); *A61K 9/06* (2013.01); *A61K 31/351* (2013.01); *A61K 31/496* (2013.01); *A61K 31/56* (2013.01); *A61K 47/10* (2013.01)

(58) Field of Classification Search
None
See application file for complete search history.

(56) References Cited

U.S. PATENT DOCUMENTS

| | | | |
|---|---|---|---|
| 2,989,965 | A | 6/1961 | Rod |
| 5,324,746 | A | 6/1994 | McKee et al. |
| 5,710,280 | A | 1/1998 | Shih et al. |
| 6,143,794 | A | 11/2000 | Chaudhuri et al. |
| 6,197,830 | B1 | 3/2001 | Frome |
| 6,365,635 | B1 | 4/2002 | Nomura |
| 9,078,853 | B2 * | 7/2015 | Ray, II .................. A61K 31/56 |
| 9,707,229 | B2 | 7/2017 | Ray |
| 9,717,748 | B2 | 8/2017 | Ray |
| 10,105,342 | B2 | 10/2018 | Ray |
| 2002/0061281 | A1 | 5/2002 | Osbakken et al. |
| 2003/0091519 | A1 | 5/2003 | Zatz et al. |
| 2003/0143162 | A1 | 7/2003 | Speirs et al. |
| 2003/0226201 | A1 | 12/2003 | Leung et al. |
| 2004/0033963 | A1 | 2/2004 | Yu et al. |
| 2004/0151765 | A1 | 8/2004 | Ritchie |
| 2004/0191329 | A1 | 9/2004 | Burrell et al. |
| 2005/0043251 | A1 | 2/2005 | Lane |
| 2005/0137164 | A1 | 6/2005 | Arkin |
| 2005/0255048 | A1 | 11/2005 | Hirsh et al. |
| 2006/0246098 | A1 | 11/2006 | Rao et al. |
| 2007/0161543 | A1 * | 7/2007 | Yu .......................... A61K 38/05 514/114 |
| 2009/0016990 | A1 | 1/2009 | Alberte et al. |
| 2010/0081669 | A1 | 4/2010 | Yang |
| 2011/0105448 | A1 | 5/2011 | Dhuppad et al. |
| 2012/0328671 | A1 | 12/2012 | O'Neil et al. |
| 2013/0072563 | A1 | 3/2013 | Ho |
| 2014/0256826 | A1 | 9/2014 | Lemire et al. |
| 2015/0320816 | A1 | 11/2015 | Patel |
| 2016/0166505 | A1 | 6/2016 | Ray |
| 2017/0035736 | A1 | 2/2017 | Ray |
| 2017/0173063 | A1 | 6/2017 | Ray |
| 2017/0239277 | A1 | 8/2017 | Ray |
| 2017/0246140 | A1 | 8/2017 | Ray |
| 2017/0312276 | A1 | 11/2017 | Ray |
| 2017/0326167 | A1 | 11/2017 | Ray |
| 2017/0333464 | A1 | 11/2017 | Ray |
| 2017/0333467 | A1 | 11/2017 | Ray |
| 2018/0036227 | A1 | 2/2018 | Ray |
| 2018/0147211 | A1 | 5/2018 | Ray |
| 2018/0147212 | A1 | 5/2018 | Ray |
| 2018/0250248 | A1 | 9/2018 | Ray |
| 2018/0256675 | A1 | 9/2018 | Ray |

FOREIGN PATENT DOCUMENTS

| | | |
|---|---|---|
| JP | H0774144 | 8/1995 |
| WO | 2006060027 | 6/2006 |
| WO | 2014167554 | 10/2014 |

OTHER PUBLICATIONS

Purvis, T., Simultaneous High Peformance Liquid Chromatography Assay of Pentoxifylline, Mupirocin, Itraconazole, and Fluticasone Propionate in Humco Lavare Wound Base, 2015, Chromatography, 2, pp. 642-654.*
Humco, https://www.humco.com/pharmaceuticals/lavare/, accessed Oct. 1, 2017.*
Kumar et al., Topical anesthesia, 2015, J Anesthesiol Clin Pharmacol, 31(4), pp. 450-456 (Year: 2015).*
Kumar et al., Clonidine for management of chronic pain: A brief review of the current evidences, 2014, Saudi J Anesth., 8(1), pp. 92-96 (Year: 2014).*
Pan et al. Urea: a comprehensive review of the clinical literature. Dermatology Online Journal, 19(11), Nov. 2013. doj_20392. Retrieved from: http://escholarship.org/uc/item/11x463rp.
Shah, "Urea ointment (40%)," Indian J Dermatol Venereol Leprol, 69:421-422, Nov. 25, 2015. Retrieved from: http://www.ijdvl.com/text.asp?2003/69/6/421/6632.
Taro Pharmaceuticals U.S.A., Inc., "U-CORT—hydrocortisone acetate cream," Mar. 2012, document of 6 pages.
PCCA, "Technical Report: Spira-Wash Gel™ Wound Care Base—an Antimicrobial Evaluation," Mar. 2014, document of 2 pages.
Crown Laboratories, "REA LO 39—urea cream," Aug. 2014, document of 4 pages.
Stratus Pharmaceuticals, Inc., "Remeven—urea cream," May 2011, document of 5 pages.
Medimetriks Pharmaceuticals, Inc., "Uramaxin GT—urea gel, Uramaxin GT—uramaxin gt and keradan," Apr. 2012, document of 11 pages.
Medimetriks Pharmaceuticals, Inc., "Uramaxin TS—urea cream," Apr. 2010, document of 6 pages.

(Continued)

*Primary Examiner* — Kortney L. Klinkel
*Assistant Examiner* — Tori Strong
(74) *Attorney, Agent, or Firm* — Akerman LLP

(57) ABSTRACT

A topical cream may include urea and one or more additional active agents such as fluticasone, itraconazole, and mupirocin. The topical cream may be formulated as a lotion, gel, ointment, foam, cream, or emulsion.

14 Claims, No Drawings

(56) References Cited

OTHER PUBLICATIONS

Crown Laboratories, "REA LO 40—urea cream, REA LO 40—urea lotion," Aug. 2014, document of 7 pages.
Angamuthu et al., "Controlled-release injectable containing Terbinafine/PLGA microspheres for Onychomycosis Treatment," 2014, Journal of Pharmaceutical Sciences, vol. 103, pp. 1178-1183. (Year: 2014).
Allen, US Pharm., 2011, vol. 36(6), pp. 44-45.
Aticlate® (Doxycycline Hyclate Tablets), Final Labeling Text, Aqua Pharmaceuticals, Revised Jul. 2014 (18 pages).
Bactroban® Ointment (mupirocin ointment, 2%) Prescribing Information, GlaxoSmithKline, Revised May 2014 (17 pages).
Bae et al., "Green Nail Syndrome Treated with the Applicatin of Tobramycin Eye Drop," 2014, Ann Dermatology, vol. 26, No. 4, pp. 514-516. (Year: 2014).
Balzarini et al., "Lancet", 2007, vol. 369, pp. 787-797.
Ciprofloxacin Human Prescription Drug Label; Physician's Desk Reference, Ver. 1—Published Feb. 2010 (19 pages) (hereinafter Ciprofloxacin PDR).
Freels, Lexington Podiatry (2011), pp. 1-2.
Iquix® PDR, Vistakon Pharmaceuticals; 6 pages (Revised Mar. 2010). (Year: 2010).
Ketoconazole Human Prescription Drug Label; Physician's Desk Reference, Ver. 1—Published Feb. 2007 (5 pages).
Kowalski et al., "Topical levofloxacin 1.5% overcomes in vitro resistance in rabbit keratitis models," Acta Ophthalmol. Jun. 2010; 88 (4): e120-e1251; cited as pp. 1-14. (Year: 2010).
Label (Package Insert) for Azithromycin, Distributed by Sicor Pharmaceuticals, Inc., Dec. 2016 (18 pages).
Label for Bactroban (mupirocin), Distributed by GlaxoSmithKline, Dec. 2015 (10 pages).
Label for Diflucan (Fluconazole Tablets), Distributed by Roerig, a Division of Pfizer, Mar. 2013 (35 pages).
Lewandowksi et al., "Military Medicine", 2013, vol. 178, pp. e503-e507.
Medinvent, "The NasoNeb Nasal Nebulizer", Nov. 15, 2013.
PCCA LoxaSperse Based Studies (2013 & 2014), pp. 1-12.
PCCA LoxaSperse, PCCA # 30-4701, 2013, pp. 1-2.
PCCA Science, "Technical Report: The Antimicrobial Activity of Itraconazole and LoxaSperse TM Against Biofilms of C. albicans," 2013, www.ccarx.com, pp. 1-2.
PCCA Xyifos Trademark Appl. No. 8842712 (May 27, 2015), pp. 1-8.
PCCA, "LoxaSperse™, Powder Excipient Base for Use in Nebulization and Irrigation Compounds," 2013, document of 3 pages.
PCCA, "New, Exclusive PCCA Base, XyliFos™: Boost the LoxaSperse™ Power in Nasal Nebulization and Decrease your Cost", Aug. 7, 2015 (2 pages).
Pfizer, "Fluconazole Injection, USP, in Intravia Plastic Container," Pfizer Injectables, Aug. 2010, document of 4 pages, https://www.pfizer.com/files/products/uspi_fluconazole.pdf.
Roerig, "Diflucan-fluconazole tablet, Diflucan-fluconazole powder, for suspension," Pfizer, Mar. 2013, document of 61 pages.
Sutherland et al., "Antimicrobial Agents and Chemotherapy," 1985, vol. 27, pp. 495-498.
Tobramycin Human Prescription Drug Label; Physician's Desk Reference, Ver. 1—Published May 2014 (9 pages).
BeyondDisease.com, "Does Bleach Kill Toenail Fungus? How to Use it?," 5 pages, available at http://www.beyonddisease.com/bleach-for-nail-fungus (published on Jun. 30, 2015).
Lee Silsby, "Loxasperse TM Formulations," 3 pages, webpage capture of http://leesilsby.com/loxasperseformulations on Oct. 17, 2014.
Bhapkar et al., IOSR Journal of Pharmacy (2013), vol. 3, pp. 24-48.

* cited by examiner

UREA CREAM FORMULATIONS

TECHNICAL FIELD

The present application is directed to compounded pharmaceutical compositions. More specifically, the present application is directed to compounded urea creams for topical treatments.

BACKGROUND

Urea is an organic compound having physiologic importance as a nitrogen carrier and osmolyte. Urea arises biologically in association with the metabolic breakdown of nitrogenous compounds or amino acids. Industrial production of urea involves conversion of ammonia and carbon dioxide to urea.

Urea has been incorporated in various cosmetic and therapeutic products intended for topical application to skin and nails. Urea creams for dermatological application have been used to treat dry or scaly skin by promoting skin hydration. The hydration or rehydration related properties of urea is also believed to aid in skin penetration. Remeven™, marketed by Stratus Pharmaceuticals Inc., FL, is an example of a urea cream including 50% urea. Rea Lo 30® or Rea Lo 40® marketed by Crown Laboratories, TN, are additional examples of urea creams that are keratolytic emollients used as skin softeners. Indicated uses for topical urea creams include eczema, ichthyosis, and dermatitis conditions. Topical urea has also been used as a penetrant agent in conjunction with other medications. U-cort®, marketed by Taro Pharmaceuticals Inc., NY, is a 1% hydrocortisone acetate cream containing urea indicated for relief of inflammatory and pruritic manifestations of corticosteroid-responsive dermatoses. U.S. Pat. No. 6,143,794 describes topical formulations claimed to be useful for treating nail fungal diseases including an antifungal compound and an excipient, which may include a keratolytic agent including urea, benzoylperoxide, salicylic acid, resorcinol, and tretinoin. Forty percent urea ointment combined with the oral or topical antifungal agent bifonazole, such as bifonazole 1% cream, has be noted for the treatment of onychomycosis (Shah M K. Urea ointment (40%). Indian J Dermatol Venereol Leprol 2003; 69:421-2).

SUMMARY

In one aspect, a method of compounding a topical cream comprises adding fluticasone, itraconazole, and mupirocin to a cream base. The fluticasone may be added in an amount such that the compounded topical cream comprises between approximately 0.5% to approximately 1.5% fluticasone by weight. The itraconazole may be added in an amount such that the compounded topical cream comprises between approximately 2.0% to approximately 5.0% itraconazole by weight. The mupirocin may be added in an amount such that the compounded topical cream comprises between approximately 2.0% to approximately 5.0% mupirocin by weight. The compounded topical cream may comprises between approximately 25% to approximately 45% urea by weight.

In one embodiment, the cream base comprises a commercially manufactured urea cream. The urea cream may comprise a urea cream selected from a 30%, 35%, 40%, 45%, or 50% urea cream. The method may further comprise adding a diluent to the cream base before, during, or after adding the fluticasone, itraconazole, and mupirocin. In one example, the compounded topical cream may comprise between approximately 0.5% fluticasone by weight, approximately 2.5% itraconazole by weight, approximately 2.5% mupirocin by weight, and approximately 25% urea by weight. In another example, the compounded topical cream comprises between approximately 0.5% fluticasone by weight, approximately 3.0% itraconazole by weight, approximately 3.0% mupirocin by weight, and approximately 35% urea by weight. In yet another example, the compounded topical cream comprises between approximately 1.0% fluticasone by weight, approximately 2.5% itraconazole by weight, approximately 5.0% mupirocin by weight, and approximately 45% urea by weight. In still yet another example, the compounded topical cream comprises between approximately 1.0% fluticasone by weight, approximately 5.0% itraconazole by weight, approximately 2.5% mupirocin by weight, and approximately 45% urea by weight. In a further example, the compounded topical cream comprises between approximately 1.0% fluticasone by weight, approximately 3.0% itraconazole by weight, approximately 3.0% mupirocin by weight, and approximately 30% urea by weight. In another further example, the compounded topical cream comprises between approximately 1.5% fluticasone by weight, approximately 2.5% itraconazole by weight, approximately 2.5% mupirocin by weight, and approximately 45% urea by weight. In yet another further example, the compounded topical cream comprises between approximately 1.0% fluticasone by weight, approximately 4.0% itraconazole by weight, approximately 3.5% mupirocin by weight, and approximately 40% urea by weight. In still yet another further example, the compounded topical cream comprises between approximately 1.5% fluticasone by weight, approximately 5.0% itraconazole by weight, approximately 5.0% mupirocin by weight, and approximately 45% urea by weight.

In one embodiment, the method further comprises adding the urea to the cream base before, during, or after adding one or more of the fluticasone, itraconazole, or mupirocin. The cream base may comprise a polyethylene glycol (PEG) based lotion, gel, ointment, foam, cream, or emulsion. One or more of the fluticasone, itraconazole, or mupirocin may be added to the cream base in powder form. The method may further comprise crushing an oral tablet comprising one or more of the fluticasone, itraconazole, or mupirocin to form a powder. Adding the fluticasone, itraconazole, and mupirocin to the cream base may comprise adding the powder to the cream base. The method may further comprises wetting the powder, wherein adding fluticasone, itraconazole, and mupirocin to the cream base comprises adding the wetted powder to the cream base.

In another aspect, a topical cream comprising a lotion, gel, ointment, foam, cream, or emulsion comprises between approximately 0.5% to approximately 1.5% fluticasone by weight, between approximately 2.0% to approximately 5.0% itraconazole by weight, between approximately 2.0% to approximately 5.0% mupirocin by weight, and between approximately 25% to approximately 45% urea by weight. The topical cream may further comprise polyethylene glycol (PEG).

DESCRIPTION

The present disclose describes pharmaceutical compositions comprising topical creams. The topical creams may be compounded topical cream comprising urea and at least one additional active agent. The additional active agent may include a steroid such as a corticoid steroid, an anti-infective such as an antibiotic, antifungal, or both. The additional active agent may also include one or more, including multiples, of an antihistamine, nerve depressant, local anesthetics, NSAIDs, anticonvulsants, antidepressants, muscle relaxants, or other active ingredients.

In various embodiments, the composition comprises a base. The base may be a base suitable for topical application to a body surface such as a foam, cream, gel, lotion, ointment, or emulsion (oil-in-water or water-in-oil), for example, suitable for topical application to skin or nails. For brevity, such bases may be referred to herein as a cream base. Thus, unless otherwise specified, a cream base may include bases comprising foams, gels, lotions, ointments, creams, or emulsions (oil-in-water or water-in-oil).

In some embodiments, the cream base comprises polyethylene glycol (PEG). In other embodiments, the cream base is PEG-free. In these or other embodiments, the cream base may comprise a silicon or silicon variant while in other embodiments the cream base may be silicon-free. An example cream base comprising a foam may include a propellant such as butane. Cream bases comprising a foam may also comprise additional characteristics such as that of an emulsion, such as an oil-in-water emulsion. In one example, the cream base comprises a cream, lotion, gel, or ointment, e.g., water soluble/miscible, absorption, water-in-oil emulsion, or oil-in-water emulsion. Example cream bases may include foams, gels, lotions, ointments, creams including or comprising hydrophilic petrolatum, white tetrolatum, hydrophilic, hydrogel, white ointment, anhydrous lanolin, hydrous lanolin, PEG, or combinations thereof.

The cream base may comprise various emollients. For example, in one embodiment the cream base comprises a keratolytic emollient. In one embodiment, the cream base may comprise one or more of acrylates copolymer, alcohol, camphor, carbomer, dimethyl isosorbide, disodium EDTA, dl-alphatocopheryl acetate, edetate disodium, emulsifying wax, eucalyptus oil, flavonoids, glycerin, glycol dicaprylate/dicaprate, hydroxyethyl cellulose, isopropyl myristate, lactic acid, meadowsweet extract, menthol, mineral oil, neopentyl, phenolic glycosides, polyethylene glycol (PEG), polysorbate 85, purified water, titanium dioxide, tridecyl stearate, tridecyl trimellitate, sodium hydroxide, sodium hydroxide, sorbitol, stearic acid, or zinc pyrithione. In various embodiments, the compounded topical composition comprises a cream base comprising a commercially available topical base. For example, in one embodiment, the compounded topical cream comprises the topical base Spira-Wash™ Gel or Lipoderm® both marketed by Professional Compounding Centers of America (PCCA), Houston, Tex.

The composition may also comprise urea. The amount of urea by weight may be between approximately 25% and approximately 45%, between approximately 25% and approximately 40%, between approximately 25% and approximately 35%, between approximately 25% and approximately 30%, between approximately 30% and approximately 45%, between approximately 30% and approximately 40%, between approximately 30% and approximately 35%, between approximately 35% and approximately 45%, between approximately 35% and approximately 40%, or between approximately 40% and approximately 45%. In these or other embodiments, the amount of urea by weight may comprises approximately 5.0%, approximately 10%, approximately 15%, approximately 20%, approximately 25%, approximately 30%, approximately 35%, approximately 40%, approximately 45%, approximately 50%, approximately 55%, or greater.

In various embodiments, the composition comprises urea in a cream base. In some such embodiments, the urea in cream base may comprise a commercially available urea cream. For example, the urea in base cream may comprise the urea cream Remeven™ marketed by Stratus Pharmaceuticals Inc. Remeven™ includes 50% urea or 500 mg urea per gram and includes acrylates copolymer, carbomer, dl— alphatocopheryl acetate, disodium EDTA, glycerin, lactic acid, mineral oil, polysorbate 85, purified water, sodium hydroxide, stearic acid and zinc pyrithione. The urea in cream base of the compounded topical cream may comprise a cream or lotion formation including a keratolytic emollient. In one embodiment, the urea in cream base comprises a urea cream including a keratolytic emollient such as Rea Lo 30® or Rea Lo 40® marketed by Crown Laboratories. Rea Lo 30® comprises 300 mg urea per gram. Rea Lo 40® comprises 400 mg urea per gram. Rea Lo includes purified water, emulsifying wax, glycerin, isopropyl myristate, sorbitol, neopentyl, glycol dicaprylate/dicaprate, tridecyl stearate, tridecyl trimellitate and dimethyl isosorbide. In another example, the urea in cream base of the compounded topical cream may comprise the urea creams Uramaxin™(45%) Cream or Lotion marketed by Medimetriks Pharmaceuticals, Inc., Fairfield, NJ or Keratol™45 Cream marketed by Breckenridge Pharmaceutical, Inc., Boca Raton, Fla.

As introduced above, the composition comprises at least one additional active agent. The additional active agent may comprise one or more agents selected from an antibacterial agent, an antiviral agent, an antifungal agent, an antibiotic agent, an anti-inflammatory agent, an non-steroidal anti-inflammatory (NSAID) agent, an anti-allergic agent, an anti-infective agent, an anti-depressant agent, a steroid agent, a stimulant agent, a disinfectant agent, an anticonvulsant agent, a local anesthetic agent, or combinations thereof.

The one or more additional actives of the composition may comprise a steroid agent comprising one or more steroid actives wherein the composition comprises a weight percent of steroid agent between approximately 0.5% to approximately 5.0%, approximately 0.5% to approximately 4.5%, approximately 0.5% to approximately 4.0%, approximately 0.5% to approximately 3.5%, approximately 0.5% to approximately 3.0%, approximately 0.5% to approximately 2.5%, approximately 0.5% to approximately 2.0%, approximately 0.5% to approximately 1.5%, approximately 0.5% to approximately 1.0%, approximately 1.0% to approximately 1.5%, approximately 1.0% to approximately 2.0%, approximately 1.0% to approximately 2.5%, approximately 1.5% to approximately 2.0%, approximately 1.5% to approximately 2.5%, approximately 2.0% to approximately 2.5%. In some such embodiments, the composition comprises, by weight, approximately 0.5%, approximately 1.0%, or approximately 1.5% corticosteroid. In one embodiment, the composition comprises a steroid agent wherein the composition comprises between approximately 0.5% to approximately 1.5% by weight steroid agent. In one embodiment, the steroid agent is or comprises one or more corticosteroids.

The steroid agent may comprise one or more steroid actives selected from fluticasone, triamcinolone, betamethasone, dexamethasone, flunisolide, prednisone, prednisolone, methylprednisolone, fluocinolone, diflorasone, halcinonide, desoximetasone, diflucortolone, flucloronide, fluocinonide, fluocortolone, fluprednidene, flurandrenolide (flurandrenolone), clobetasol, clobetasone, alclometasone, flumethasone, fluocortolone, amcinonide, beclometasone, difluprednate, prednicarbate, flurandrenolide, mometasone, desonide, or combinations thereof. In one embodiment, the steroid agent is or comprises the steroid active fluticasone wherein the composition comprises approximately 0.5% to approximately 1.5% by weight fluticasone.

The one or more active agents of the composition may comprise an antifungal agent comprising one or more antifungal actives. According to various embodiments, the composition comprises a weight percent of antifungal agent between approximately 1.5% to approximately 6.0%, approximately 1.5% to approximately 5.5%, approximately 1.5% to approximately 5.0%, approximately 1.5% to approximately 4.5%, approximately 1.5% to approximately 4.0%, approximately 1.5% to approximately 3.5%, approximately 1.5% to approximately 3.0%, approximately 1.5% to approximately 2.5%, approximately 1.5% to approximately 2.0%, approximately 2.0% to approximately 6.0%, approximately 2.0% to approximately 5.5%, approximately 2.0% to approximately 5.0%, approximately 2.0% to approximately 4.5%, approximately 2.0% to approximately 4.0%, approximately 2.0% to approximately 3.5%, approximately 2.0% to approximately 3.0%, approximately 2.0% to approximately 2.5%, approximately 2.5% to approximately 6.0%, approximately 2.5% to approximately 5.5%, approximately 2.5% to approximately 5.0%, approximately 2.5% to approximately 4.5%, approximately 2.5% to approximately 4.0%, approximately 2.5% to approximately 3.5%, approximately 2.5% to approximately 3.0%, approximately 3.0% to approximately 6.0%, approximately 3.0% to approximately 5.5%, approximately 3.0% to approximately 5.0%, approximately 3.0% to approximately 4.5%, approximately 3.0% to approximately 4.0%, approximately 3.0% to approximately 3.5%, approximately 3.5% to approximately 6.0%, approximately 3.5% to approximately 5.5%, approximately 3.5% to approximately 5.0%, approximately 3.5% to approximately 4.5%, approximately 3.5% to approximately 4.0%, approximately 4.0% to approximately 6.0%, approximately 4.0% to approximately 5.5%, approximately 4.0% to approximately 5.0%, approximately 4.0% to approximately 4.5%, approximately 4.5% to approximately 6.0%, approximately 4.5% to approximately 5.5%, approximately 4.5% to approximately 5.0%, approximately 5.0% to approximately 6.0%, approximately 5.0% to approximately 5.5%. In some such embodiments, the composition comprises, by weight, approximately 2.0%, approximately 2.5%, or approximately 3.0%, approximately 3.5%, approximately 4.0%, approximately 4.5%, or approximately 5.0% antifungal agent. In some formulations, the antifungal agent is or comprises an azole. The azole may include itraconazole, for example. Itraconazole may be added alone or in combination with additional antifungal actives. Other azoles may include clotrimazole, econazole, oxiconazole, ketoconazole, miconazole, voriconazole, sulconazole, fluconazole. In the above or other formulations, the antifungal agent may comprise one or more antifungal actives selected from ciclopirox, amphotericin B, Nystatin, terbinafine, amorolfine, flucytosine, or combination thereof. In one embodiment, the composition comprises between approximately 2.0% to approximately 5.0% antifungal agent by weight wherein the antifungal agent is or comprises the antifungal active itraconazole.

The one or more additional active agents may comprise an antibiotic agent comprising one or more antibiotic actives. According to various embodiments, the composition comprises a weight percent of antibiotic agent between approximately 1.5% to approximately 6.0%, approximately 1.5% to approximately 5.5%, approximately 1.5% to approximately 5.0%, approximately 1.5% to approximately 4.5%, approximately 1.5% to approximately 4.0%, approximately 1.5% to approximately 3.5%, approximately 1.5% to approximately 3.0%, approximately 1.5% to approximately 2.5%, approximately 1.5% to approximately 2.0%, approximately 2.0% to approximately 6.0%, approximately 2.0% to approximately 5.5%, approximately 2.0% to approximately 5.0%, approximately 2.0% to approximately 4.5%, approximately 2.0% to approximately 4.0%, approximately 2.0% to approximately 3.5%, approximately 2.0% to approximately 3.0%, approximately 2.0% to approximately 2.5%, approximately 2.5% to approximately 6.0%, approximately 2.5% to approximately 5.5%, approximately 2.5% to approximately 5.0%, approximately 2.5% to approximately 4.5%, approximately 2.5% to approximately 4.0%, approximately 2.5% to approximately 3.5%, approximately 2.5% to approximately 3.0%, approximately 3.0% to approximately 6.0%, approximately 3.0% to approximately 5.5%, approximately 3.0% to approximately 5.0%, approximately 3.0% to approximately 4.5%, approximately 3.0% to approximately 4.0%, approximately 3.0% to approximately 3.5%, approximately 3.5% to approximately 6.0%, approximately 3.5% to approximately 5.5%, approximately 3.5% to approximately 5.0%, approximately 3.5% to approximately 4.5%, approximately 3.5% to approximately 4.0%, approximately 4.0% to approximately 6.0%, approximately 4.0% to approximately 5.5%, approximately 4.0% to approximately 5.0%, approximately 4.0% to approximately 4.5%, approximately 4.5% to approximately 6.0%, approximately 4.5% to approximately 5.5%, approximately 4.5% to approximately 5.0%, approximately 5.0% to approximately 6.0%, approximately 5.0% to approximately 5.5%. In some such embodiments, the composition comprises, by weight, approximately 2.0%, approximately 2.5%, or approximately 3.0%, approximately 3.5%, approximately 4.0%, approximately 4.5%, or approximately 5.0% antibiotic agent.

The antibiotic agent may comprise one or more antibiotic actives comprising amikacin, amoxicillin, gentamicin, kanamycin, neomycin, netilmicin, paromomycin, tobramycin, geldanamycin, herbimycin, carbacephem (loracarbef), ertapenem, doripenem, imipenem, cefadroxil, cefazolin, cefalotin, cephalexin, cefaclor, cefamandole, cefoxitin, cefprozil, cefuroxime, cefixime, cefdinir, cefditoren, cefoperazone, cefotaxime, cefpodoxime, ceftazidime, ceftibuten, ceftizoxime, ceftriaxone, cefepime, ceftobiprole, clarithromycin, clavulanic acid, clindamycin, colistimethate teicoplanin, azithromycin, dirithromycin, erythromycin, troleandomycin, telithromycin, aztreonam, ampicillin, azlocillin, bacampicillin, carbenicillin, cloxacillin, dicloxacillin, flucloxacillin, mezlocillin, meticillin, nafcillin, norfloxacin, oxacillin, penicillin G, penicillin V, piperacillin, pvampicillin, pivmecillinam, ticarcillin, bacitracin, colistin, colimycin, polymyxin B, ciprofloxacin, enoxacin, gatifloxacin, levofloxacin, lomefloxacin, moxifloxacin, ofloxacin, trovafloxacin, grepafloxacin, sparfloxacin, afenide, prontosil, sulfacetamide, metronidazole, sulfamethizole, sulfanilimide, sulfamethoxazole, sulfisoxazole, trimethoprim, trimethoprim-sulfamethoxazole, demeclocycline, doxycycline, oxytetracycline, tetracycline, arsphenamine, chloramphenicol, chlorhexidine, lincomycin, ethambutol, fosfomycin, furazolidone, isoniazid, linezolid, mupirocin, nitrofurantoin, platensimycin, pyrazinamide, quinupristin/dalfopristin, rifampin, thiamphenicol, rifampicin, minocycline, sultamicillin, sulbactam, sulphonamides, mitomycin, spectinomycin, spiramycin, roxithromycin, meropenem, or combination thereof. In one formulation, the antibiotic agent is or comprises the antibiotic active mupirocin wherein the composition comprises between approximately 2.0% to approximately 5.0% antibiotic agent by weight.

In various embodiments, the composition includes a steroid agent comprising a corticosteroid active comprising fluiticasone or one or more corticosteroid agents in addition to or instead of fluticasone selected from budesonide, betamethasone, triamcinolone, or combination thereof. In this or another formulation, the composition also includes an antifungal agent comprising an antifungal active comprising itraconazole or one or more antifungal actives in addition to or instead of itraconazole selected from amphotericin, fluconazole, voriconazole, or combination thereof. In any of the above formulations or in another variation, the composition may include an antibiotic agent comprising an antibiotic active comprising mupirocin or one or more antibiotic actives in addition to or instead of mupirocin selected from clindamycin, besifloxacin, cefazolin, ofloxacin, azithromycin, ceftazidime, natamycin, ciprofloxacin, gentamicin, vancomycin, tobramycin, clarithromycin, levofloxacin, moxifloxacin, Nystatin, or combination thereof.

In various embodiments, the composition as described herein comprises active agents in addition to the steroid, antifungal, or antibiotic agents. For example, in one embodiment, the composition further comprises a local anesthetic agent. The local anesthetic agent may comprise one or more local anesthetic actives selected from lidocaine, amethocaine, benzocaine, prilocaine, or combination thereof. In one formulation, the composition comprises between approximately 0.5% to approximately 5.0% local anesthetic agent by weight. In this or another variation, the composition further comprises a non-steroidal anti-inflammatory (NSAID) agent. The NSAID agent may comprise one or more NSAID actives selected from indomethacin, ibuprofen, dexibuprophen, diclofenac, ketoprofen, flurbiprofen, piroxicam, pranoprofen lidocaine, amethocaine, benzocaine, prilocaine, or combination thereof. In one formulation, composition may comprise approximately 0.5% to approximately 5.0% NSAID agent by weight. In one embodiment, the compounded topical cream comprises approximately 0.5% to approximately 1.5% fluticasone by weight, approximately 2% to approximately 5% itraconazole by weight, approximately 2% to approximately 5% itraconazole by weight, approximately 25% to approximately 45% urea by weight, and approximately 0.05% to approximately 1.0% amitriptyline, capsacin, diltiazem, clonidine, nefedipin, pentoxifylline, emedastine, gabapentin, ketamine, ketotifen, or rebamipide.

In various embodiments, the composition comprises a base cream including between approximately 25% to approximately 45% urea by weight and additional active agents with at least two additional active agents selected from a steroid agent, antifungal agent, or antibiotic agent, wherein the composition comprises between approximately 0.5% to approximately 1.5% by weight steroid agent, approximately 2.0% to approximately 5.0% by weight antifungal agent, and approximately 2.0% to approximately 5.0% antibiotic agent. The steroid agent may comprise one or more corticosteroid actives selected from budesonide, betamethasone, triamcinolone, or combination thereof. The antifungal agent may comprise one or more antifungal actives selected from amphotericin, fluconazole, voriconazole, or combination thereof, the antibiotic agent may comprise one or more antibiotic actives selected from clindamycin, besifloxacin, cefazolin, ofloxacin, azithromycin, ceftazidime, natamycin, ciprofloxacin, gentamicin, vancomycin, tobramycin, clarithromycin, levofloxacin, moxifloxacin, Nystatin, or combination thereof. In further embodiments, the additional active agents further comprise at least one agent selected from a local anesthetic agent and a non-steroidal anti-inflammatory (NSAID) agent. The local anesthetic agent may comprise one or more local anesthetic actives selected from lidocaine, amethocaine, benzocaine, prilocaine, or combination thereof. In one formulation, the composition comprises between approximately 0.5% to approximately 5.0% local anesthetic agent by weight. The NSAID agent may comprise one or more NSAID actives selected from indomethacin, ibuprofen, dexibuprophen, diclofenac, ketoprofen, flurbiprofen, piroxicam, pranoprofen lidocaine, amethocaine, benzocaine, prilocaine, or combination thereof. In one formulation, the composition may comprise approximately 0.5% to approximately 5.0% NSAID agent by weight. Additional active agents may also be included.

In various embodiments, the composition comprises a base cream including between approximately 25% to approximately 45% urea by weight and additional active agents with at least two additional active agents selected from a steroid agent, antifungal agent, or antibiotic agent, wherein the steroid agent is or comprises the steroid active fluticasone and the composition comprises between approximately 0.5% to approximately 1.5% by weight steroid agent, wherein the antifungal agent is or comprises itraconazole and the composition comprises between approximately 2.0% to approximately 5.0% by weight antifungal agent, and wherein the antibiotic agent is or comprises the antibiotic active mupirocin and the composition comprises between approximately 2.0% to approximately 5.0% antibiotic agent. In one such embodiment, the additional active agents include the steroid agent, antifungal agent, and antibiotic agent. In further embodiments, the additional active agents further comprise at least one agent selected from a local anesthetic agent and a non-steroidal anti-inflammatory (NSAID) agent. The local anesthetic agent may comprise one or more local anesthetic actives selected from lidocaine, amethocaine, benzocaine, prilocaine, or combination thereof. In one formulation, the composition comprises between approximately 0.5% to approximately 5.0% local anesthetic agent by weight. The NSAID agent may comprise one or more NSAID actives selected from indomethacin, ibuprofen, dexibuprophen, diclofenac, ketoprofen, flurbiprofen, piroxicam, pranoprofen lidocaine, amethocaine, benzocaine, prilocaine, or combination thereof. In one formulation, composition may comprise approximately 0.5% to approximately 5.0% NSAID agent by weight. Additional active agents may also be included.

In various embodiments, a method of making the herein described compositions include compounding the active agents to form a compounded topical cream. For example, making the compounded topical cream may comprise adding urea and the one or more additional active agents to a cream base. In one embodiment, the additional active agents may be compounded with urea in cream base wherein the urea is added to the cream base prior to, during, or after the one or more additional actives. In another embodiment, the urea in cream base comprises a pre-mixed urea cream, e.g., in the form of a commercial composition as introduced above. The urea cream may comprise a PEG based gel, ointment, lotion, foam, cream, or emulsion, for example. The urea creams may comprise various percentages of urea by weight prior to compounding such as 5%, 10%, 15%, 20%, 25%, 30%, 35%, 40%, 45%, 50%, 55%, or greater. It is to be understood that urea creams may be supplemented with urea, diluted, or cut prior to or, in some embodiments, after compounding the urea cream with additional actives. Thus the compounded composition may comprise more or less urea by weight than was present in the urea cream prior to compounding. Urea may be added to the cream base in an amount or the urea cream may be adjusted such that the compounded topical cream comprises between approximately 25% and approximately 45%, between approximately 25% and approximately 40%, between approximately 25% and approximately 35%, between approximately 25% and approximately 30%, between approximately 30% and approximately 45%, between approximately 30% and approximately 40%, between approximately 30% and approximately 35%, between approximately 35% and approximately 45%, between approximately 35% and approximately 40%, or between approximately 40% and approximately 45% urea by weight.

One or more additional active agents may be added to the cream base, which may include urea in the cream base (added to the cream base or a commercial urea cream) or the cream base without urea. The one or more additional active agents may include one or more members of the active agent classes comprising steroids, antifungals, antibiotics, or combination thereof.

The steroid agent may comprise one or more steroid actives, as introduced above, which may be added individually or may be added in combination with the other steroid actives or members of other active agent classes. The steroid agent may be added in an amount such that the compounded topical cream comprises approximately 0.5% to approximately 5.0%, approximately 0.5% to approximately 4.5%, approximately 0.5% to approximately 4.0%, approximately 0.5% to approximately 3.5%, approximately 0.5% to approximately 3.0%, approximately 0.5% to approximately 2.5%, approximately 0.5% to approximately 2.0%, approximately 0.5% to approximately 1.5%, approximately 0.5% to approximately 1.0%, approximately 1.0% to approximately 1.5%, approximately 1.0% to approximately 2.0%, approximately 1.0% to approximately 2.5%, approximately 1.5% to approximately 2.0%, approximately 1.5% to approximately 2.5%, approximately 2.0% to approximately 2.5% steroid agent. In some such embodiments, the compounded topical cream comprises approximately 0.5%, approximately 1.0%, or approximately 1.5% steroid agent.

The antifungal agent may comprise one or more antifungal actives, as introduced above, which may be added individually or may be added in combination with the other antifungal actives or members of other active agent classes. The antifungal agent may be added an amount such that the compounded topical cream comprises 1.5% to approximately 6.0%, approximately 1.5% to approximately 5.5%, approximately 1.5% to approximately 5.0%, approximately 1.5% to approximately 4.5%, approximately 1.5% to approximately 4.0%, approximately 1.5% to approximately 3.5%, approximately 1.5% to approximately 3.0%, approximately 1.5% to approximately 2.5%, approximately 1.5% to approximately 2.0%, approximately 2.0% to approximately 6.0%, approximately 2.0% to approximately 5.5%, approximately 2.0% to approximately 5.0%, approximately 2.0% to approximately 4.5%, approximately 2.0% to approximately 4.0%, approximately 2.0% to approximately 3.5%, approximately 2.0% to approximately 3.0%, approximately 2.0% to approximately 2.5%, approximately 2.5% to approximately 6.0%, approximately 2.5% to approximately 5.5%, approximately 2.5% to approximately 5.0%, approximately 2.5% to approximately 4.5%, approximately 2.5% to approximately 4.0%, approximately 2.5% to approximately 3.5%, approximately 2.5% to approximately 3.0%, approximately 3.0% to approximately 6.0%, approximately 3.0% to approximately 5.5%, approximately 3.0% to approximately 5.0%, approximately 3.0% to approximately 4.5%, approximately 3.0% to approximately 4.0%, approximately 3.0% to approximately 3.5%, approximately 3.5% to approximately 6.0%, approximately 3.5% to approximately 5.5%, approximately 3.5% to approximately 5.0%, approximately 3.5% to approximately 4.5%, approximately 3.5% to approximately 4.0%, approximately 4.0% to approximately 6.0%, approximately 4.0% to approximately 5.5%, approximately 4.0% to approximately 5.0%, approximately 4.0% to approximately 4.5%, approximately 4.5% to approximately 6.0%, approximately 4.5% to approximately 5.5%, approximately 4.5% to approximately 5.0%, approximately 5.0% to approximately 6.0%, approximately 5.0% to approximately 5.5%. In some such embodiments, the composition comprises approximately 2.0%, approximately 2.5%, or approximately 3.0%, approximately 3.5%, approximately 4.0%, approximately 4.5%, or approximately 5.0% antifungal agent.

The antibiotic agent may comprise one or more antibiotic actives, as introduced above, which may be added individually or may be added in combination with the other antibiotic actives or members of other active agent classes. The antibiotic agent may be added to the cream in an amount such that the compounded topical cream comprises approximately 1.5% to approximately 6.0%, approximately 1.5% to approximately 5.5%, approximately 1.5% to approximately 5.0%, approximately 1.5% to approximately 4.5%, approximately 1.5% to approximately 4.0%, approximately 1.5% to approximately 3.5%, approximately 1.5% to approximately 3.0%, approximately 1.5% to approximately 2.5%, approximately 1.5% to approximately 2.0%, approximately 2.0% to approximately 6.0%, approximately 2.0% to approximately 5.5%, approximately 2.0% to approximately 5.0%, approximately 2.0% to approximately 4.5%, approximately 2.0% to approximately 4.0%, approximately 2.0% to approximately 3.5%, approximately 2.0% to approximately 3.0%, approximately 2.0% to approximately 2.5%, approximately 2.5% to approximately 6.0%, approximately 2.5% to approximately 5.5%, approximately 2.5% to approximately 5.0%, approximately 2.5% to approximately 4.5%, approximately 2.5% to approximately 4.0%, approximately 2.5% to approximately 3.5%, approximately 2.5% to approximately 3.0%, approximately 3.0% to approximately 6.0%, approximately 3.0% to approximately 5.5%, approximately 3.0% to approximately 5.0%, approximately 3.0% to approximately 4.5%, approximately 3.0% to approximately 4.0%, approximately 3.0% to approximately 3.5%, approximately 3.5% to approximately 6.0%, approximately 3.5% to approximately 5.5%, approximately 3.5% to approximately 5.0%, approximately 3.5% to approximately 4.5%, approximately 3.5% to approximately 4.0%, approximately 4.0% to approximately 6.0%, approximately 4.0% to approximately 5.5%, approximately 4.0% to approximately 5.0%, approximately 4.0% to approximately 4.5%, approximately 4.5% to approximately 6.0%, approximately 4.5% to approximately 5.5%, approximately 4.5% to approximately 5.0%, approximately 5.0% to approximately 6.0%, approximately 5.0% to approximately 5.5%. In some such embodiments, the compounded topical cream comprises approximately 2.0%, approximately 2.5%, or approximately 3.0%, approximately 3.5%, approximately 4.0%, approximately 4.5%, or approximately 5.0% antibiotic agent.

The actives may be obtained from commercial dosage forms or from bulk sources. The actives may be added to the cream in dry form or within solution or suspension when added to the cream base, urea in cream base, or urea cream. For example, one or more of the actives may be in powder form obtained from a bulk source or by crushing oral tablets. The powder may be wetted with a wetting agent comprising an organic or aqueous medium prior to addition to the cream. Example wetting agents may include dimethyl sulfoxide (DMSO), an alcohol, water, e.g., purified water, water for irrigation, water for injection, or a sterile water. The one or more additional actives may be folded into the cream base, urea in cream base, or urea cream or mixed therein using a mixer, or both. The cream base, urea in cream base, or urea cream combined with one or more of the one or more additional actives may be processed through an ointment mill and then packaged in tubes, pouches, or another suitable container. The size of the container may be configured to contain an amount of the compounded topical cream comprising a single or multiple dosages.

The urea in cream base or urea cream may be diluted or cut by addition of a suitable diluent before, during, or after one or more additional actives are added. The diluent may comprise a cream base that is the same or different than the original cream base or base component of the urea cream.

In one embodiment, a method of compounding a topical cream comprises forming a topical cream comprising urea and one or more active agents including one or more members of the active agent classes comprising steroids, antifungals, antibiotics, or combination thereof. In one variation, the method may include adding the corticosteroid fluticasone, the antifungal itraconazole, and the antibiotic mupirocin to a cream base or urea cream. The fluticasone may be added in an amount sufficient to obtain approximately 0.5% to approximately 5.0%, approximately 0.5% to approximately 4.5%, approximately 0.5% to approximately 4.0%, approximately 0.5% to approximately 3.5%, approximately 0.5% to approximately 3.0%, approximately 0.5% to approximately 2.5%, approximately 0.5% to approximately 2.0%, approximately 0.5% to approximately 1.5%, approximately 0.5% to approximately 1.0%, approximately 1.0% to approximately 1.5%, approximately 1.0% to approximately 2.0%, approximately 1.0% to approximately 2.5%, approximately 1.5% to approximately 2.0%, approximately 1.5% to approximately 2.5%, approximately 2.0% to approximately 2.5%, approximately 0.5%, approximately 1.0%, or approximately 1.5% by weight fluticasone. The itraconazole and mupirocin may each be added to the cream such that the cream comprises approximately 1.5% to approximately 6.0%, approximately 1.5% to approximately 5.5%, approximately 1.5% to approximately 5.0%, approximately 1.5% to approximately 4.5%, approximately 1.5% to approximately 4.0%, approximately 1.5% to approximately 3.5%, approximately 1.5% to approximately 3.0%, approximately 1.5% to approximately 2.5%, approximately 1.5% to approximately 2.0%, approximately 2.0% to approximately 6.0%, approximately 2.0% to approximately 5.5%, approximately 2.0% to approximately 5.0%, approximately 2.0% to approximately 4.5%, approximately 2.0% to approximately 4.0%, approximately 2.0% to approximately 3.5%, approximately 2.0% to approximately 3.0%, approximately 2.0% to approximately 2.5%, approximately 2.5% to approximately 6.0%, approximately 2.5% to approximately 5.5%, approximately 2.5% to approximately 5.0%, approximately 2.5% to approximately 4.5%, approximately 2.5% to approximately 4.0%, approximately 2.5% to approximately 3.5%, approximately 2.5% to approximately 3.0%, approximately 3.0% to approximately 6.0%, approximately 3.0% to approximately 5.5%, approximately 3.0% to approximately 5.0%, approximately 3.0% to approximately 4.5%, approximately 3.0% to approximately 4.0%, approximately 3.0% to approximately 3.5%, approximately 3.5% to approximately 6.0%, approximately 3.5% to approximately 5.5%, approximately 3.5% to approximately 5.0%, approximately 3.5% to approximately 4.5%, approximately 3.5% to approximately 4.0%, approximately 4.0% to approximately 6.0%, approximately 4.0% to approximately 5.5%, approximately 4.0% to approximately 5.0%, approximately 4.0% to approximately 4.5%, approximately 4.5% to approximately 6.0%, approximately 4.5% to approximately 5.5%, approximately 4.5% to approximately 5.0%, approximately 5.0% to approximately 6.0%, approximately 5.0% to approximately 5.5%, approximately 2.0%, approximately 2.5%, approximately 3.0%, approximately 3.5%, approximately 4.0%, approximately 4.5%, or approximately 5.0% by weight of each of itraconazole and mupirocin wherein the percent by weight of itraconazole and the percent by weight of mupirocin may be the same or different. In one embodiment, the percent by weight mupirocin is greater than the percent by weight itraconazole while in another embodiment the percent by weight of itraconazole is greater than the percent by weight of mupirocin.

The urea may be added to the cream base in an amount or the cream base may comprise a urea cream adjustable such that the compounded topical cream comprises between approximately 25% and approximately 45%, between approximately 25% and approximately 40%, between approximately 25% and approximately 35%, between approximately 25% and approximately 30%, between approximately 30% and approximately 45%, between approximately 30% and approximately 40%, between approximately 30% and approximately 35%, between approximately 35% and approximately 45%, between approximately 35% and approximately 40%, or between approximately 40% and approximately 45% urea by weight.

In one embodiment, the fluticasone is added to the cream in an amount such that the compounded topical cream comprises between approximately 0.5% to approximately 1.5% fluticasone by weight, the itraconazole is added in an amount such that the compounded topical cream comprises between approximately 2.0% to approximately 5.0% itraconazole by weight, and the mupirocin is added in an amount such that the compounded topical cream comprises between approximately 2.0% to approximately 5.0% itraconazole by weight. The compounded topical cream may comprise approximately 25% and approximately 45%, between approximately 25% and approximately 40%, between approximately 25% and approximately 35%, between approximately 25% and approximately 30%, between approximately 30% and approximately 45%, between approximately 30% and approximately 40%, between approximately 30% and approximately 35%, between approximately 35% and approximately 45%, between approximately 35% and approximately 40%, or between approximately 40% and approximately 45% urea by weight. The urea may be added to the cream base before, during, or after adding one or more of the fluticasone, itraconazole, or mupirocin. The cream base may comprise a polyethylene glycol (PEG) based lotion, gel, ointment, foam, cream, or emulsion. One or more of fluticasone, itraconazole, or mupirocin may be added to the cream base, urea in cream base, or urea cream in powder form. The powder may be obtained from a bulk source, e.g., pure, or, in some embodiments, by crushing one or more oral tablets comprising one or more of fluticasone, itraconazole, or mupirocin to form the powder. The powder may be added to the cream base, which, depending on the embodiment, may already include urea or urea may be added subsequently. In these or other embodiments, the powder may be wetted with a wetting agent. The wetting agent may comprise dimethyl sulfoxide (DMSO), an alcohol, water, e.g., purified water, water for irrigation, water for injection, or a sterile water. The wetted powder may be added to the cream base, urea in cream base, or urea cream. In one embodiment, the actives fluticasone, itraconazole, and mupirocin are added to the cream base where the cream base comprises a commercially manufactured urea cream. The urea cream may comprise a urea cream selected from a 30%, 35%, 40%, 45%, or 50% urea cream. The urea cream may include a keratolytic emollient. In one such embodiment, the urea cream comprises Rea Lo 30® or Rea Lo 40®. A diluent may be added to the cream base or urea cream to adjust or modify concentration of actives in the compounded topical cream before, during, or after adding the fluticasone, itraconazole, and mupirocin.

In further embodiments, one or more of the additional active agents comprising the steroid, antifungal, or antibiotic agent may comprise one or more additional actives added to the cream. For example, in one embodiment, the steroid agent further includes a corticosteroid active selected from budesonide, betamethasone, triamcinolone, or combination thereof. In this or another variation, the antifungal agent further includes an antifungal active selected from amphotericin, fluconazole, voriconazole, or combination thereof. In any of the above variations or in another variation, the antibiotic agent further includes an antibiotic active selected from clindamycin, besifloxacin, cefazolin, ofloxacin, azithromycin, ceftazidime, natamycin, ciprofloxacin, gentamicin, vancomycin, tobramycin, clarithromycin, levofloxacin, moxifloxacin, Nystatin, or a combination thereof.

In various embodiments, the method of compounding the topical cream comprises adding still additional active agents to the cream in addition to the steroid, antifungal, and antibiotic agent. For example, in one embodiment, the method comprises adding a local anesthetic agent. The local anesthetic agent may comprise one or more local anesthetic actives selected from lidocaine, amethocaine, benzocaine, prilocaine, or combination thereof. The local anesthetic agent may be added to approximately 0.5% to approximately 5.0% of the compounded topical cream by weight. In this or another variation, the method comprises adding a non-steroidal anti-inflammatory (NSAID) agent. The NSAID agent may comprise one or more NSAID actives selected from indomethacin, ibuprofen, dexibuprofen, diclofenac, ketoprofen, flurbiprofen, piroxicam, pranoprofen lidocaine, amethocaine, benzocaine, prilocaine, or combination thereof. The NSAID agent may be added to approximately 0.5% to approximately 5.0% of the compounded topical cream by weight. In one embodiment, the compounded topical cream comprises approximately 0.5% to approximately 1.5% fluticasone by weight, approximately 2% to approximately 5% itraconazole by weight, approximately 2% to approximately 5% itraconazole by weight, approximately 25% to approximately 35% urea by weight, and approximately 0.05% to approximately 1.0% amitriptyline, capsacin, diltiazem, clonidine, nefedipin, pentoxifylline, emedastine, gabapentin, ketamine, ketotifen, or rebamipide.

This specification has been written with reference to various non-limiting and non-exhaustive embodiments. However, it will be recognized by persons having ordinary skill in the art that various substitutions, modifications, or combinations of any of the disclosed embodiments (or portions thereof) may be made within the scope of this specification. Thus, it is contemplated and understood that this specification supports additional embodiments not expressly set forth in this specification. Such embodiments may be obtained, for example, by combining, modifying, or reorganizing any of the disclosed steps, components, elements, features, aspects, characteristics, limitations, and the like, of the various non-limiting and non-exhaustive embodiments described in this specification. In this manner, Applicant reserves the right to amend the claims during prosecution to add features as variously described in this specification, and such amendments comply with the requirements of 35 U.S.C. §§ 112(a) and 132(a).

The grammatical articles "one", "a", "an", and "the", as used in this specification, are intended to include "at least one" or "one or more", unless otherwise indicated. Thus, the articles are used in this specification to refer to one or more than one (i.e., to "at least one") of the grammatical objects of the article. By way of example, "a component" means one or more components, and thus, possibly, more than one component is contemplated and may be employed or used in an application of the described embodiments. Further, the use of a singular noun includes the plural, and the use of a plural noun includes the singular, unless the context of the usage requires otherwise. Additionally, the grammatical conjunctions "and" and "or" are used herein according to accepted usage. By way of example, "x and y" refers to "x" and "y". On the other hand, "x or y" refers to "x", "y", or both "x" and "y", whereas "either x or y" refers to exclusivity.

The present disclosure may be embodied in other forms without departing from the spirit or essential attributes thereof and, accordingly, reference should be had to the following claims rather than the foregoing specification as indicating the scope of the invention. Further, the illustrations of arrangements described herein are intended to provide a general understanding of the various embodiments, and they are not intended to serve as a complete description. Many other arrangements will be apparent to those of skill in the art upon reviewing the above description. Other arrangements may be utilized and derived therefrom, such that logical substitutions and changes may be made without departing from the scope of this disclosure.

The Abstract of the Disclosure is provided to comply with 37 C.F.R. § 1.72(b), requiring an abstract that will allow the reader to quickly ascertain the nature of the technical disclosure. It is submitted with the understanding that it will not be used to interpret or limit the scope or meaning of the claims.

What is claimed is:

1. A method of compounding a topical cream, the method comprising:
    adding fluticasone, itraconazole, and mupirocin to a cream base,
    wherein fluticasone is added in an amount such that the compounded topical cream comprises between approximately 0.5% to approximately 1.5% fluticasone by weight,
    wherein itraconazole is added in an amount such that the compounded topical cream comprises between approximately 2.0% to approximately 5.0% itraconazole by weight,
    wherein mupirocin is added in an amount such that the compounded topical cream comprises between approximately 2.0% to approximately 5.0% mupirocin by weight,
    wherein the cream base comprises a commercially manufactured urea cream selected from a 30%, 35%, 40%, 45%, or 50% urea cream,
    wherein the compounded topical cream comprises between approximately 25% to approximately 45% urea by weight, and
    wherein the compounded topical cream further comprises between approximately 0.5% to approximately 5.0% amethocaine or benzocaine, by weight, and between approximately 0.05% to approximately 1.0% amitriptyline, capsacin, diltiazem, nefedipin, emedastine, gabapentin, ketamine, ketotifen, or rebamipide by weight.

2. The method of claim 1, further comprising adding a diluent to the cream base before, during, or after adding the fluticasone, itraconazole, and mupirocin.

3. The method of claim 1, wherein the compounded topical cream comprises between approximately 0.5% fluticasone by weight, approximately 2.5% itraconazole by weight, approximately 2.5% mupirocin by weight, and approximately 25% urea by weight.

4. The method of claim 1, wherein the compounded topical cream comprises between approximately 0.5% fluticasone by weight, approximately 3.0% itraconazole by weight, approximately 3.0% mupirocin by weight, and approximately 35% urea by weight.

5. The method of claim 1, wherein the compounded topical cream comprises between approximately 1.0% fluticasone by weight, approximately 2.5% itraconazole by weight, approximately 5.0% mupirocin by weight, and approximately 45% urea by weight.

6. The method of claim 1, wherein the compounded topical cream comprises between approximately 1.0% fluticasone by weight, approximately 5.0% itraconazole by weight, approximately 2.5% mupirocin by weight, and approximately 45% urea by weight.

7. The method of claim 1, wherein the compounded topical cream comprises between approximately 1.0% fluticasone by weight, approximately 3.0% itraconazole by weight, approximately 3.0% mupirocin by weight, and approximately 30% urea by weight.

8. The method of claim 1, wherein the compounded topical cream comprises between approximately 1.5% fluticasone by weight, approximately 2.5% itraconazole by weight, approximately 2.5% mupirocin by weight, and approximately 45% urea by weight.

9. The method of claim 1, wherein the compounded topical cream comprises between approximately 1.0% fluticasone by weight, approximately 4.0% itraconazole by weight, approximately 3.5% mupirocin by weight, and approximately 40% urea by weight.

10. The method of claim 1, wherein the compounded topical cream comprises between approximately 1.5% fluticasone by weight, approximately 5.0% itraconazole by weight, approximately 5.0% mupirocin by weight, and approximately 45% urea by weight.

11. The method of claim 1, wherein one or more of the fluticasone, itraconazole, and mupirocin is added to the cream base in powder form.

12. The method of claim 1, further comprising crushing an oral tablet comprising one or more of the fluticasone, itraconazole, and mupirocin to form a powder.

13. The method of claim 12, wherein adding the fluticasone, itraconazole, and mupirocin to the cream base comprises adding the powder to the cream base.

14. The method of claim 12, further comprising wetting the powder, wherein adding fluticasone, itraconazole, and mupirocin to a cream base comprises adding the wetted powder to the cream base.

* * * * *